US00PP08114P

United States Patent [19]

Ilsink

[11] Patent Number: Plant 8,114

[45] Date of Patent: Jan. 26, 1993

[54] ROSE PLANT INTERNIKI

[75] Inventor: Peter Ilsink, Leersum, Netherlands

[73] Assignee: Bear Creek Gardens, Inc., Medford, Oreg.

[21] Appl. No.: 715,342

[22] Filed: Jun. 14, 1991

[51] Int. Cl.[5] ..... A01H 5/00
[52] U.S. Cl. ..... Plt./28
[58] Field of Search ..... Plt. 28, 29

[56] References Cited

U.S. PATENT DOCUMENTS

P.P. 3,070 10/1971 McGredy ..... Plt. 28

*Primary Examiner*—Howard J. Locker
*Attorney, Agent, or Firm*—Klarquist, Sparkman, Campbell, Leigh & Whinston

[57] ABSTRACT

A floribunda rose plant having the ability to produce, in the greenhouse, small, red, simultaneously opening flowers borne in clusters, high production of cut flowers (200 stems with flower clusters per square meter), resistance to powdery mildew, good vase life, and vigorous upright growth habit.

1 Drawing Sheet

The present invention relates to a new and distinct variety of rose plant of the floribunda class which was originated by me by crossing an unnamed seedling with an unnamed seedling.

The primary objective of this breeding was to produce a new rose variety having high production of simultaneously opening reddish blooms, preferably borne in clusters; mildew resistance; and long vase lift. The objective was substantially achieved along with other desirable improvements as evidenced by the following unique combination of characteristics which are outstanding in the new variety and which distinguish it from its parents, as well as from all other varieties of which I am aware:

1. The ability, in a greenhouse environment, to produce simultaneously opening flowers.
2. Small, red blooms borne in clusters.
3. High production of cut flowers (about 200 stems with flower clusters per square meter).
4. Resistance to powdery mildew.
5. Good vase life.
6. Vigorous upright growth habit.

Asexual reproduction of this new variety by budding, as performed at Wasco and Somis, Calif., shows that the foregoing characteristics and distinctions come true to form and are established and transmitted through succeeding propagations.

The accompanying color photograph shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:
*Seed parent.*—Unnamed seedling.
*Pollen parent.*—Unnamed seedling.

Classification:
*Botanical.*—Rosa hybrida.
*Commercial.*—Floribunda.

FLOWER

Observations made from specimens grown a greenhouse environment in Somis, Calif. from January, 1990, to February, 1991.

Blooming habit: Recurrent.

Bud:
*Size.*—$\frac{7}{8}$ inch when the petals start to unfurl.
*Form.*—Short, blunt and topped.
*Color.*—When sepals first divide, bud color is Red Group 42A. When half blown, the upper sides of the petals are Red Group 42A; and the lower sides of the petals are Red Group 42A.
*Sepals.*—Color: Green Group 138B. Surface texture: Covered with many very fine hairs. There are three normally appendaged sepals. There are two unappendaged sepals with hairy edges.
*Receptacle.*—Color: Green Group 137C. Shape: Funnel. Size: Small ($\frac{1}{4}$ inch$\times\frac{1}{4}$ inch). Surface: Smooth.
*Peduncle.*—Length: Short ($1\frac{1}{2}$ inches to $1\frac{3}{4}$ inches). Surface: Smooth with an occasional small prickle and gland. Color: Medium green. Strength: Stiff, erect.

Bloom:
*Size.*—Small. Average open size is $2\frac{1}{2}$ inches.
*Borne.*—Several together, in rounded to flat clusters.
*Stems.*—Medium, strong (14 to 18 inches long).
*Form.*—When first open: Has high center. Permanence: Bloom retains its form to the end; outer petals curl back with some quilling.
*Petalage.*—Number of petals under normal conditions: 35 to 40.
*Color.*—The upper side of the petals is Red Group 42A. The reverse side of the petals is Red Group 42A. The color of the base of petals intensifies to a distinct greenish white half moon at the point of attachment ($\frac{1}{4}$ inch$\times\frac{1}{4}$ inch) at the petal base. The major color on the upper side is Red Group 42A.

*Variegations.*—Occasional white streak on the guard petals.

*Discoloration.*—No general tonality color change at the end of the first day, and no change at the end of the third day.

*Fragrance.*—None.

Petals:

*Texture.*—Thick, leathery.

*Shape.*—Round.

*Form.*—Tips slightly recurved, edges slightly quilled.

*Arrangement.*—Imbricated, with few petaloids in the center.

*Persistence.*—Hang on and dry.

*Lastingness.*—On the plant: Long (5 to 7 days). As a cut flower; Long (7 to 8 days).

Reproductive parts:

*Anthers.*—Size: Medium. Quantity: Many. Color: Yellow. Arrangement: Regular around styles.

*Filaments.*—Color: Yellow.

*Pollen.*—Color: Lemon yellow.

*Styles.*—Color: White.

*Stigmas.*—Color: Greenish white.

Form: Bush.

Growth: Vigorous, upright, branching.

Foliage: Number of leaflets on normal mid-stem leaves: 5.

*Size.*—Medium (5 inches long×3 inches wide).

*Quantity.*—Abundant.

*Color.*—New foliage: Green. Old foliage: Dark green and glossy.

Leaflets:

*Shape.*—Pointed oval.

*Texture.*—Upper side: Leathery, glossy.

*Edge.*—Serrated.

*Serration.*—Single, small.

*Petiole rachis.*—Color: Green with some reddish color on upper rachis in young leaves.

*Petiole underside.*—Smooth with an occasional prickle.

*Stipules.*—Medium, bearded.

*Disease resistance.*—Resistant to mildew under normal growing conditions at Somis, Calif. This variety is a greenhouse cut flower and has not been tested for blackspot or rust resistance.

Wood:

*New wood.*—Color: Light green. Bark: Smooth.

*Old wood.*—Color: Green Bark: Smooth.

Prickles:

*Quantity.*—Ordinary number on main canes from base and on laterals from main canes.

*Form.*—Medium, hooked downward.

*Color when young.*—Red.

Small prickles:

*Quantity.*—None on main stalks or on laterals.

I claim:

1. A new and distinct variety of rose plant of the floribunda class, substantially as herein shown and described, characterized particularly as to novelty by the unique combination of its ability to produce many flowering stems per square meter, each flowering stem producing a cluster of small red flowers that open simultaneously, a good vase life as a cut flower, resistance to powdery mildew, and a vigorous upright growth habit.

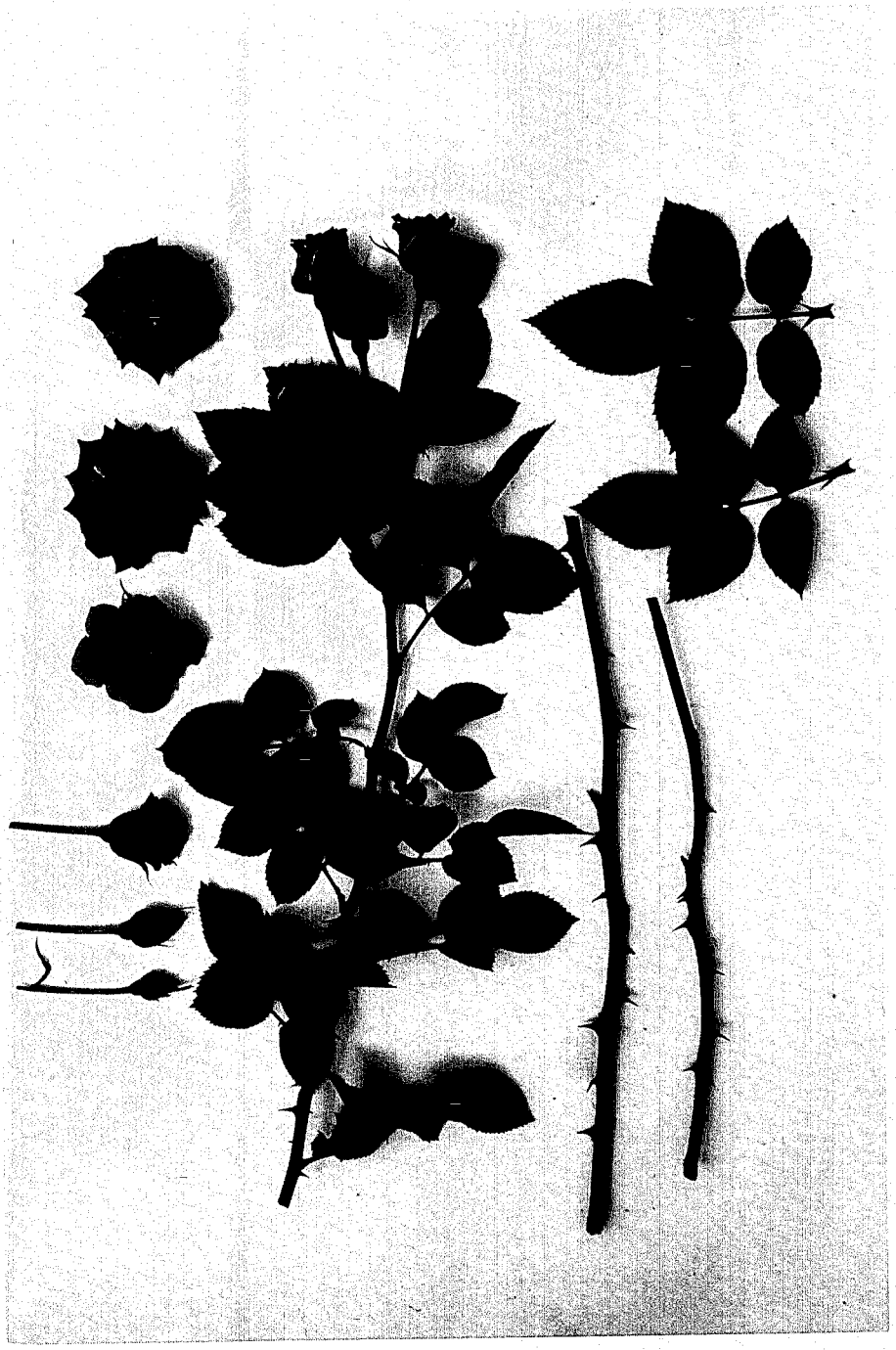

* * * * *